US009326974B2

(12) United States Patent
Thompson et al.

(10) Patent No.: US 9,326,974 B2
(45) Date of Patent: May 3, 2016

(54) METHODS AND RELATED COMPOSITIONS FOR THE TREATMENT OF CANCER

(71) Applicant: STC.UNM, Albuquerque, NM (US)

(72) Inventors: Todd A. Thompson, Albuquerque, NM (US); Debra Mackenzie, Albuquerque, NM (US); Tudor I. Oprea, Albuquerque, NM (US); Larry A. Sklar, Albuquerque, NM (US); Bruce S. Edwards, Albuquerque, NM (US); Mark Haynes, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/449,957

(22) Filed: Aug. 1, 2014

(65) Prior Publication Data

US 2014/0343347 A1 Nov. 20, 2014

Related U.S. Application Data

(62) Division of application No. 12/990,334, filed as application No. PCT/US2009/003438 on Jun. 5, 2009, now Pat. No. 8,835,506.

(60) Provisional application No. 61/131,015, filed on Jun. 5, 2008.

(51) Int. Cl.
| | |
|---|---|
| A01N 43/66 | (2006.01) |
| A61K 31/437 | (2006.01) |
| A61K 31/165 | (2006.01) |
| A61K 31/445 | (2006.01) |
| A61K 31/135 | (2006.01) |
| A61K 45/06 | (2006.01) |
| A61N 5/10 | (2006.01) |

(52) U.S. Cl.
CPC ............ *A61K 31/437* (2013.01); *A61K 31/135* (2013.01); *A61K 31/165* (2013.01); *A61K 31/445* (2013.01); *A61K 45/06* (2013.01); *A61N 5/10* (2013.01)

(58) Field of Classification Search
None
See application file for complete search history.

(56) References Cited

U.S. PATENT DOCUMENTS

| | | | |
|---|---|---|---|
| 4,593,031 A | 6/1986 | Griffith et al. | |
| 6,093,704 A | 7/2000 | Nickel et al. | |
| 8,287,851 B2 | 10/2012 | Wright et al. | |
| 8,314,077 B2 | 11/2012 | Webb et al. | |
| 8,338,464 B2 | 12/2012 | Melnick et al. | |
| 8,362,075 B2 | 1/2013 | Lewis et al. | |
| 8,420,665 B2 | 4/2013 | Huang et al. | |
| 8,835,506 B2* | 9/2014 | Thompson et al. | 514/656 |
| 2005/0019378 A1* | 1/2005 | Zhang | A61K 9/0014 424/443 |
| 2010/0285001 A1 | 11/2010 | Land et al. | |

FOREIGN PATENT DOCUMENTS

| | | |
|---|---|---|
| EP | 1466628 A1 | 10/2004 |
| WO | 9734589 | 9/1997 |
| WO | 9744063 | 11/1997 |
| WO | 0024395 | 5/2000 |
| WO | 0071135 A1 | 11/2000 |
| WO | 0189520 A2 | 11/2001 |
| WO | 0217904 A1 | 3/2002 |
| WO | 0238164 A1 | 5/2002 |
| WO | 2008108986 A2 | 9/2008 |
| WO | 2008113364 A2 | 9/2008 |
| WO | 2008148798 A2 | 12/2008 |
| WO | 2008151257 A2 | 12/2008 |
| WO | 2009029206 A1 | 3/2009 |
| WO | 2009045443 A2 | 4/2009 |
| WO | 2009076629 A2 | 6/2009 |
| WO | 2009088838 A2 | 7/2009 |
| WO | 2011130429 A2 | 10/2011 |

OTHER PUBLICATIONS

Zhang et al. Direct Identification of Coxiella burnetii Plasmids in Human Sera by Nested PCR. J Clin Microbiol 1998, vol. 36, No. 8, pp. 2210-2213.*
Lubick et al. Securinine, a GABAA receptor antagonist, enhances macrophage clearance of phase II C. burnetii: comparison with TLR agonists. J Leukocyte Biology, Nov. 2007. vol. 82, pp. 1062-1069.*
Delaney et al. The Role of Radiotherapy in Cancer Treatment. Estimating Optimal Utilization from a Review of Evidence-Based Clinical Guidelines. Cancer. ACS, Aug. 3, 2005. vol. 104, Issue 6, pp. 1129-1137.*
Tatematsu et al. Cytotoxic Principles of Securinega virosa: Virosecurinine and Viroallosecurinine and Related Derivatives. J Pharm Sci, 1991, vol. 80, No. 4, pp. 325-327.*
Dong et al. Securinine induced apoptosis in human leukemia HL-60 cells. Acta Pharmacol Sin, 1999. vol. 20, No. 3, pp. 267-270.*
Yedjou et al. Dose- and Time-Dependent Response of Human Leukemia (HL-60) Cells to Arsenic Trioxide Treatment. Int J Environ Res Public Health, 2006. vol. 3, No. 2, pp. 136-140.*

(Continued)

*Primary Examiner* — Marcela M Cordero Garcia
(74) *Attorney, Agent, or Firm* — Henry D. Coleman; R. Neil Sudol

(57) ABSTRACT

A method of treatment and/or prevention of cancer comprises administering agents which cause increased intracellular granularity in cancer cells, at least in an amount sufficient to inhibit proliferation of such cells and preferably in an amount sufficient to lead to cancer cell death. The method is particularly directed to refractory cancer, particularly hormone refractory prostate cancer. The agents identified cause increased intracellular granularity in the cancer cells, and also convert adherent cancer cells to non-adherent cancer cells, leading to cancer cell death. Using the present invention, cancer cells undergo increased intracellular granularity at relatively low agent concentrations, while also inhibiting cell proliferation. Increased concentrations lead to conversion of adherent cancer cells to non-adherent cancer cells, then to cell death. While the exact mechanism of cancer cell degradation and death is not completely understood, the treated cancer cells, including refractory prostate cancer cells, give indications of cell death through an autophagic mechanism. Pharmaceutical compositions related to the presently disclosed methods are also disclosed.

29 Claims, 4 Drawing Sheets

(56) References Cited

OTHER PUBLICATIONS

Brandes LJ, et al. Stimulation of Malignant Growth in Rodents by Antidepressant Drugs at Clinically Relevant Doses. Cancer Research, 1992;52:3796-3800.
Parker KA, et al. The effect of tricyclic antidepressants on cutaneous melanoma cell lines and primary cell cultures. Anti-Cancer Drugs, 2012;22:65-69.
Hammack JE, et al. Phase III evaluation of nortriptyline for alleviation of symptons of cis-platinum-induced peripheral neuropathy. Pain, 2002;98:195-203.
Wolf S, et al. Chemotherapy-induced peripheral neuropathy: Prevention and treatment strategies. European Journal of Cancer, 2008;44:1507-1515.
Kautio AL, et al. Amitriptyline in the Prevention of Chemotherapy-induced Neuropathic Symptoms. Anticancer Research, 2009;29:2601-2606.
Kaley TJ, Deangelis LM. Therapy of chemotherapy-induced peripheral neuropathy.
Levy, Michael. Drug Therapy. Pharmacologic Treatment of Cancer Pain. New England Journal of Medicine, 1996:1124-1132.
Mousa AM, et al. Disseminated pelvic hydatidosis presenting as ovarian carcinomatosis: successful post-operative treatment with mebendazole. Int J Gynaecol Obstet, 1987:25(6):473-478.
Mukhopadhyay T, Sasaki J, Ramesh R, Roth JA. Mebendazole elicits a potent antitumor effect on human cancer cell lines both in vitro and in vivo. Clin Cancer Res, 2002;8(9):2963-2969.
Sasaki J, et al. The anthelmintic drug mebendazole induces mitotic arrest and apoptosis by depolymerizing tubulin in non-small cell lung cancer cells. Mol Cancer Ther, 2002;1(13):1201-1209.
Martarelli D, Pompei P, Baldi C, Mazzoni G. Mebendazole inhibits growth of human adrenocortical carcinoma cell lines implanted in nude mice. Cancer Cemother Pharmacol, 2008;61(5):809-817.
Doudican N, Rodriguez A, Osman I, Orlow SJ. Mebendazole induces apoptosis via Bcl-2 inactivation in chemoresistant melanoma cells. Mol Cancer Res, 2008;6(8):1308-1315.
Spagnuolo PA, et al. The antihelmintic flubendazole inhibits microtubule function through a mechanism distinct from Vinca alkaloids and displays preclinical activity in leukemia and myeloma. Blood, 2010;115(23):4824-4833.
Dobrosotskaya IY, et al. Mebendazole monotherapy and long-term disease control in metastatic adrenocortical carcinoma. Endocr Pract, 2011;17(3):e59-e62.
Bai RY, et al. Antiparasitic mebendazole shows survival benefit in 2 preclinical models of glioblastoma multiforme. Neuro Oncol, 2011;13(9):974-982.
Mackenzie D, et al. High-throughput screening of small molecule inducers of autophagy as potential therapies for prostate cancer. Proc Am Assoc cancer Res, 2009;18-22.
Dennis MK, et al. A Multifunction Androgen Receptor Screening Assay Using the High-Throughput HyperCyt(R) Flow Cytometry System. Cytometry Part A, 2008;73A:390-399.
Haynes MK, et al. Detection of Intracellular Granularity Induction in Prostate Cancer Cell Lines by Small Molecules Using the HyperCyt(R) High-Throughput Flow Cytometry System. Journal of Biomolecular Screening, 2009;14:596-609.
Patel K, Doudican NA, Schiff PB, Orlow SJ. Albendazole sensitized cancer cells to ionizing radiation. Radiat Oncol, 2011;6:160.
Belaz KR, et al. Enantiomeric resolution of albendazole sulfoxide by semipreparative HPLC and in vitro study of growth inhibitory effects on human cancer cell lines. J Pharm Biomed Anal, 2012;66:100-108.
Choi EK, et al. Differential effect of intraperitoneal albendazole and paclitaxel on ascites formation and expression of vascular endothelial growth factor in ovarian cancer cell-bearing athymic nude mice. Reprod Sci, 2011;18(8):763-771.
Kim Y, Pourgholami MH, Morris DL, Stenzel MH. An optimized RGD-decorated micellar drug delivery system for albendazole for the treatment of ovarian cancer: from RAFT polymer synthesis to cellular uptake. Macromol Biosci, 2001;11(2):219-233.
Pourgholami MH, et al. Potent inhibition of tumoral hypoxia-inducible factor 1 alpha by albendazole. BMC Cancer, 2010;10:143.
Pourgholami MH, Cai ZY, Chu SW, Galettis P, Morris DL. The influence of ovarian cancer induced peritoneal carinomatosis on the pharmacokinetics of albendazole in nude mice. Anticancer Res, 2010;30(2):423-428.
Pourgholami MH, et al. Phase I clinical trail to determine maximum tolerated dose of oral albendazole in patients with advanced cancer. Cancer Chemother Pharmacol, 2010;65(3):597-605.
Chu SW, Bader S, Morris DL, Pourgholami MH. Potent inhibition of tubulin polymerisation and proliferation of paclitaxel-resistant 1A9PTX22 human ovarian cancer cells by albendazole. Anticancer Res, 2009;29(10):3791-3796.
Pourgholami MH, et al. Inhibition of cell proliferation, vascular endothelial growth factor and tumor growth by albendazole. Cancer Invest, 2009;27(2):171-177.
Zhao Y, et al. Solubilisation and cytotoxicity of albendazole encapsulated in cucurbit[n]uril. Org Biomol Chem, 2008;6(24):4509-4515.
Pourgholami MH, Wangoo KT, Morris DL. Albendazole-cyclodextrin complex: enhanced cytotoxicity in ovarian cancer cells. Anticancer Res, 2008;28(5A):2775-2779.
Pourgholami MH, et al. Albendazole: a potent inhibitor of vascular endothelial growth factor and malignant ascites formation on OVCAR-3 tumor-bearing nude mice. Clin Cancer Res, 2006;12(6):1928-1935.
Merino G, et al. Transport of anthelmintic benzimidazole drugs by breast cancer resistance protein (BCRP/ABCG2). Drug Metab Dispos, 2005;33(5):614-618.
Pourgholami MH, Akhter J, Wang L, Lu Y, Morris DL. Antitumor activity of albendazole against the human colorectal cancer cell line HT-29: invitro and in a xenograft model of peritoneal carcinomatosis. Cancer Chemother Pharmacol, 2005;55(5):425-432.
Morris DL, Jourdan JL, Pourgholami MH. Pilot study of albendazole in patients with advanced malignancy. Effect on serum tumor markers/high incidence of neutropenia. Oncology, 2001;61(1):42-46.
Pourgholami MH, et al. In vitro and in vivo suppression of growth of hepatocellular carcinoma cells by albendazole. Cancer Lett, 2001;165(1):43-49.
Del Brutto OH. The use of albendazole in patients with single lesions enhanced on contrast CT. N Engl J Med, 1993;328(5):356-357.
Ayub M, Levell MJ. Inhibition of testicular 17 alpha-hydroxylase and 17,20-lyase by not 3 beta-hydroxysteroid dehydrogenase-isomerase or 17 beta-hydroxysteroid oxidoreductase by ketoconazole and other imidazole drugs. J Steroid Biochem, 1987;28(5):521-531.
Brandes LJ, et al. Enhanced cancer growth in mice administered daily human-equivalent doses of some H1-antihistimines: predictive in vitro correlates. J Natl Cancer Inst, 1994;86(10):770-775.
Robinson A. More questions than answers: antihistamines' link to cancer. CMAJ, 1994;151(6):797-801.
Kurokawa M, Futamura Y, Obata M, Shibutani Y. Re: Enhanced cancer growth in mice administered daily human-equivalent doses of some H1-antihistimines: predictive in vitro correlates. J Natl Cancer Inst, 1995;87(21):1638-1639.
Benze J, et al. Carcinogenicity studies of astemizole in mice and rats. Cancer Res, 1995;55(23):5589-5594.
Platz EA. A Novel Two-Stage, Transdisciplinary Study Identifies Digoxin as a possible Drug for Prostate Cancer Treatment. Cancer Discov, 2011;1:68-77.
Niraula S, et al. Influence of concurrent medications on outcomes of men with prostate cancer cancer included in the TAX 327 study. Can Urol Assoc J, 2011;2:1-8.
Juang JJ, Lin YF, Chang PL, Tsui KH. Cardiac glycosides derease prostate specific antigen expression by down-regulation of prostate derived Ets factor. J Urol, 2010;184(5):2158-2164.
Lin J, Denmeade S, Carducci MA. HIF-1alpha and calcium signaling as targets for treatment of prostate cancer by cardiac glycosides. Curr Cancer Drug Targets, 2009;9(7):881-887.
Simpson CD, et al. Inhibition of the sodium potassium adenosine triphosphatase pump sensitizes cancer cells to anoikis and prevents distant tumor formation. Cancer Res, 2009;69(7):2739-2747.
Beheshti Zavareh R, et al. Inhibition of the sodium/oitassium ATPase impairs N-glycan expression and function. Cancer Res, 2008;68(16):6688-6697.

(56) References Cited

OTHER PUBLICATIONS

Lin H, Juang JL, Wang PS. Involvement of Cdk5/p25 in digoxin-triggered prostate cancer cell apoptosis. J Biol Chem, 2004;279(28):29302-29307.
Yeh JY, Huang WJ, Kan SF, Wang PS. Inhibitory effects of digitalis on the proliferation of androgen dependent and independent prostate cancer cells. J Urol, 2001;166(5):1937-1942.
McConkey DJ, et al. Cardiac glycosides stimulate Ca2+ increases and apoptosis in androgen-independent, metastatic human prostate adenocarcinoma cells. Cancer Res, 2000;60(14):3807-3812.
Gao P, Dang CV, Watson J. Unexpected antitumorigenic effect of fenbendazole when combined with supplementary vitamins. J Am Assoc Lab Anim Sci, 2008;47(6):37-40.
Merino G, et al. Transport of anthelmintic benzimidazole drugs by breast cancer resistance protein (BCRP/ABCG2) Drug Metab Dispos, 2005;33(5):614-618.
Shoda T, et al. Liver tumor promoting effects of fenbendazole in rats. Toxicol Pathol, 1999;27(5):553-562.
Tsuruo T, et al. Effects of quinidine and related compounds on cytotoxicity and cellular accumulation of vincristine and Adriamycin in drug-resistant tumor cells. Cancer Research, 1984;44:4303-4307.
Zhang Z, et al. The application of epigenetic modifiers on the treatment of prostate and bladder cancer. Urologic Oncology, 2006;24:152-160.
Wang CZ, et al. Potential role of ginseng in the treatment of colorectal cancer. American Journal of Chinese Medicine, 2008;36:1019.
Castaldo S, et al. Propolis, an old remedy used in modern medicine. Fitoterapia, 2002;73(Supplement 1):S1-S6.
Hui L, et al. The combined effects of antibacterial peptide cecropin A and anti-cancer agents on leukemia cells. Anticancer Research, 2002;22:2811-2816.
Tamim HM, et al. Antidepressants and risk of prostate cancer: a nested case-control study. Prostate Cancer Prostatic Dis, 2008;11:53-60.
Cotterchio M, et al. Antidepressant medication use and breast cancer risk. Am J Epidemiology, 2000;151:951-957.
Magni G, et al. Antidepressants in the treatment of cancer pain: a survey in Italy. Pain, 1987;29:347-353.
Yoshida M, et al. Histone deacetylase as a new target for cancer chemotherapy. Cancer Chemotherapy and Pharmacology, 2001;48(Supplement 1):S20-S26.
Gupta K, et al. Antimitotic antifungal compound benomyl inhibits brain microtubule polymerization and dynamics and cancer cell proliferation at mitosis by binding to a novel site in tubulin. Biochemistry, 2004;43:6645-6655.
Smith CD, et al. Cryptophycin: a new antimicrotubule agent active against drug-resistant cells. Cancer Research, 1994; 54:3779-3784.
Merino G, et al. Transport of anthelmintic benzimidazole drugs by breast cancer resistance eprotein (BCRP/ABCG2). Drug Metab Dispos, 2005;33:614-618.
Sasaki JI, et al. The anthelmintic drug mebendazole induces mitotic arrest and apoptosis by depolymerizing tubulin in non-small cell lung cancer cells. Molecular Cancer Therapeutics, 2002;1:1201-1209.
Yu DH, et al. Pyrvinium targets the unfolded protein response to hypoglycemia and its anti-tumor activity is enhanved by combination therapy. PLoS One, 2008;3:e3951.

Wargovich MJ, et al. Efficacy of potential chemopreventive agents on rat colon aberrant crypt formation and progression. Carcinogenesis, 2000;21:1149-1155.
Piccart MJ, et al. Corticosteroids significantly delay the onset of docetaxel-induced fluid retention: final results of a randomized study of the European Organization of Research and Treatment of Cancer Investigational Drug Branch for Breast Cancer. J Clin Oncology, 1997;15:3149-3255.
Ferrante K, et al. Promising new developments in cancer chemotherapy. Cancer Chemother Pharmacol, 1999;43: S61-S66.
Roy MK, et al. Antiproliferative effect on human cancer cell lines after treatment with nimbolide extracted from an edible part of the neem tree (*Azadirachta indica*). Phytotherapy Res, 2007;21:245-250.
Martirosyan AR, et al. Differentiation-inducing quinolones as experimental breast cancer agents in the MCF-7 human breast cancer cell model. Biochem Pharmacol, 2004;68:1729-1738.
Nallan L, et al. Protein farnesyltransferase inhibitors exhibit potent antimalarial activity. J Med Chem, 2005;48:3704-3713.
Choi JH, et al. Potential inhibition of PDK1/Akt signaling by phenothiazines suppresses cancer cell proliferation and survival; Ann NY Acad Sci, 2008;38:393-403.
Azuine MA, et al. Cancer chemopreventive effect of phenothiazines and related tri-heterocyclic analogues in the 12-O-tetradecanoylphorbol-13-acetate promoted Epstein-Bar Virus early antigen activation and the mouse skin two-stage carcinogenesis models. Pharmacol Res, 2004;49:161-169.
Kim MS, et al. N-methyl-D-aspartate receptor type 2B is epigenetically inactivated and exhibits tumor-suppressive activity in human esophageal cancer. Cancer Research, 2006;66:3409-3418.
Tetef M, et al. Mitomycin C and menadione for the treatment of lung cancer: a phase II trial. Invest New Drugs, 1995;13:157-162.
Lewis A, et al. Treatment of pancreatic cancer cells with dicumarol induces cytotoxicity and oxidative stress. Clin Cancer Res, 2004;10:4550-4558.
Huang Z, et al. Impact of liver P450 reductase suppression on cyclophosphamide activation, pharmacokinetics and antitumoral activity in a cytochrome P450-based cancer gene therapy model. Cancer Gene Ther, 2000;7:1034-1042.
Dilman VM, et al. Potentiation of antitumor effect of cyclophosphamide and hydrazine sulfate by treatment weith the antidiabetic agent, 1-phenylethylbiguanide (phenformin). Cancer Lett, 1979;7:357-361.
Wolf I, et al. Diabetes mellitus and breast cancer, Lancet Oncol, 2005;6:103-111.
Brouqui P, et al. Letter to the Editor: Chronic Coxiella burnetii Infection Mimicking Malignant Hematologic Disease. American Journal of Hematology, 1992;39:309.
Capo C, et al. Coxiella bunetii Avoids Macrophage Phagocytosis by Interfering with Spatial Disrtibution of Complement Receptor 3. J Immunol, 2003;170:4217-4225.
Ito K. Prostate cancer in Asian men. Nat Rev Urol, 2014;11:197-212.
Lipton JH, et al. Q Fever Inflammatory Pseudotumor of the Lung. Chest, 1987;92(4):756-757.
Ramos HS, et al. Q Fever: Report of a Case Simulating Lymphoma. Case Reports, 1957;47(5)1030-1035.
Voth DE et al. Coxiella burnetii Inhibits Apoptosis Human THP-1 Cells and Monkey Primary Alveolar Macrophages. Infection and Immunity, 2007;75(9):4263-4271.

\* cited by examiner

METHODS AND RELATED COMPOSITIONS FOR THE TREATMENT OF CANCER

CROSS REFERENCE TO RELATED APPLICATIONS

This application is a division of U.S. patent application Ser. No. 12/990,334 of identical title, filed Mar. 11, 2011, now U.S. Pat. No. 8,835,506,which is a U.S. national stage application based upon and claiming priority from International Patent Application No. PCT/US2009/003438, filed Jun. 5,2009, of identical title, which claims priority in U.S. Provisional Patent Application No. 61/131,015, filed Jun. 5, 2008, all of which applications are incorporated by reference in their entirety herein.

FEDERALLY SPONSORED RESEARCH

The present invention was made with government support under Grant No. 1U54 MH074425-01PI, awarded by the National Institute of Health. As a result, the Government has certain rights in the invention.

FIELD OF INVENTION

This invention relates to a method for preventing and/or treating cancer using therapeutic compositions containing compounds which induce increased cellular granularity, and conversion of cancer cells from adherent to non-adherent, leading to cancer cell death.

BACKGROUND OF THE INVENTION

Cancer is a multifaceted disease characterized by an increase in the number of abnormal cells derived from a given normal tissue, with these cells typically invading adjacent tissues, or metastasizing by spreading through the blood to other regions of the body. Cancer typically progresses through a multistep process that begins with minor preneoplastic changes, which may progress to neoplasia, the neoplastic lesions possibly developing an increasing capacity for invasion, growth, metastasis, and heterogeneity.

There is an enormous variety of cancers, with examples including cancer of the lung, colon, rectum, prostate, breast, brain, and intestine. The incidence of cancer continues to climb as the general population ages, as new cancers develop, and as susceptible populations grow. A tremendous demand exists for new methods and compositions that can be used to treat patients with cancer.

As a one specific example, most men will in their lifetime experience problems that stem from diseases in their prostate. Malignancies of the prostate gland are the most common form of cancer to occur among men in the United States, affecting over 180,000 men.

Current therapy may involve surgery, chemotherapy, hormonal therapy and/or radiation treatment to eradicate neoplastic cells in a patient. Other therapies involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

When prostate cancer is diagnosed prior to metastasis, the patient has a greater then 99% chance of survival. The most successful means for treating prostate cancer at this stage is a radical prostatectomy. Unfortunately, this surgery carries with it the risk of severing nerves and blood vessels associated with sexual organs and the bladder, and can potentially result in impotency or incontinency. Radiation therapy is yet another commonly used procedure that carries the risk of impotency. Half the patients who undergo radiation therapy for prostate cancer become impotent within 2 years of treatment. In addition to the adverse affects associated with these procedures, they are significantly less effective in patients whose cancer has already delocalized or metastasized on diagnosis. In these cases, patients generally undergo even more invasive procedures such as hormonal therapy or chemotherapy. Unfortunately, most patients eventually stop responding to hormonal therapy and the most successful chemotherapeutic, Taxotere, only prolongs the life of advanced prostate cancer patients by 2.5 months on average.

As another alternative therapeutic, monoclonal antibody (mAb)-based immunotherapy has proven clinically beneficial for cancer patients while allowing them to maintain a good quality of life. These antibodies can either regulate proliferation of cancer cells through the manipulation of signal transduction, or promote cytotoxicity. Two examples of FDA-approved mAb-based anticancer drugs are Herceptin and Rituxan (Rituximab), which are currently being used for the treatment of breast cancer and non-Hodgkin's lymphoma, respectively. While there are no mAb-based therapeutics currently available for prostate cancer patients, advanced clinical studies on mAb-based immunotherapy has shown promise for the treatment of prostate cancer including advanced prostate cancer. Despite the major advantages of mAb-based immunotherapy, there are significant pitfalls which may limit its potential. In general, mAb-based therapeutics are highly costly ($70,000 for full course of treatment of Herceptin), lack oral bioavailability, and can lead to severe and often fatal side-effects. For example, Herceptin is associated with heart problems and cannot be administered to approximately 10% of cancer patients because of heart-related complications. Rituxan can cause several side-effects which include renal failure, infections and immune and pulmonary toxicity.

Overall, chemotherapy often has many drawbacks. Many chemotherapeutic agents are toxic to healthy cells, and chemotherapy can cause significant and dangerous side effects, including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by a different mechanism from the drugs used in the specific treatment. This phenomenon is referred to as pleiotropic drug or multidrug resistance. Because of such drug resistance, many cancers prove refractory to standard chemotherapeutic treatment protocols.

For example, while treatments for prostate cancer do exist, over time prostate cancer can become refractory to the treatments, and once refractory, there are few options available for treating advanced, hormone refractory prostate cancer. Consequently, it is of vital importance to identify new methods of cancer prevention and treatment, particularly against refractory cancer cells.

SUMMARY OF THE INVENTION

It is an object of the present invention to identify compounds that are useful in the treatment of cancer.

It is a further object to provide methods of treatment and/or prevention of cancer comprising administering agents which cause increased intracellular granularity in cancer cells, at least in an amount sufficient to inhibit proliferation of such cells and preferably in an amount sufficient to lead to cancer cell death.

It is yet another object to provide a method of treatment for cancer, including refractory cancer, particularly prostate cancer including hormone refractory prostate cancer, as well as metastatic prostate cancer by administering agents which cause increased intracellular granularity in the refractory cancer cells, at least in an amount sufficient to inhibit proliferation of such cells and preferably in an amount sufficient to lead to refractory cancer cell death. This method may optionally utilize radiation therapy to treat cancer in combination with the agents of the present invention, which also exhibit radiosensitizing activity.

It is another object to provide a method for treating cancer, including refractory cancer, particularly prostate cancer including hormone refractory prostate cancer, as well as metastatic prostate cancer by administering agents which cause increased intracellular granularity in the refractory cancer cells, at least in an amount sufficient to inhibit proliferation of such cells and preferably in an amount sufficient to lead to refractory cancer cell death, in combination with one or more secondary anticancer agents or other agents which are effective in treating cancer, especially prostate cancer, including metastatic prostate cancer as otherwise described herein and further in combination with a pharmaceutically acceptable carrier, additive or excipient. Optionally, radiation therapy may be combined with the anticancer included in this method to take advantage of the radiosensitizer activity of anticancer agents of the present invention.

It is still another object of the invention to provide pharmaceutical compositions which comprise primary anticancer agents which cause increased intracellular granularity in cancer cells, especially refractory cancer cells, as otherwise disclosed herein in combination with a secondary anticancer agent or other agent which is found to be useful in treating cancer, especially prostate cancer, including metastatic prostate cancer as otherwise described herein and further in combination with a pharmaceutically acceptable carrier, additive or excipient.

Without being limited by way of theory, [0014] Tthese and other objects of the present invention are achieved by a method which comprises administering to a mammal an effective amount of a composition as otherwise described herein sufficient for increasing the intracellular granularity of cancer cells, thereby inhibiting cell proliferation and preferably in an amount sufficient to cause cancer cell death. In addition, the inventive method further comprises administering a composition in an amount effective for converting adherent cancer cells to non-adherent cancer cells, leading to cancer cell death.

Using the present invention, cancer cells undergo increased intracellular granularity at relatively low concentrations of the inventive compositions, while also inhibiting cell proliferation. Increased concentrations lead to conversion of adherent cancer cells to non-adherent cancer cells, then to cell death. While the exact mechanism of cancer cell degradation and death is not completely understood, the treated cancer cells, including refractory prostate cancer cells, do not produce indications of apoptotic cell death, but rather give indications of cell death through an autophagic mechanism.

DETAILED DESCRIPTION OF THE INVENTION

Figure 1:
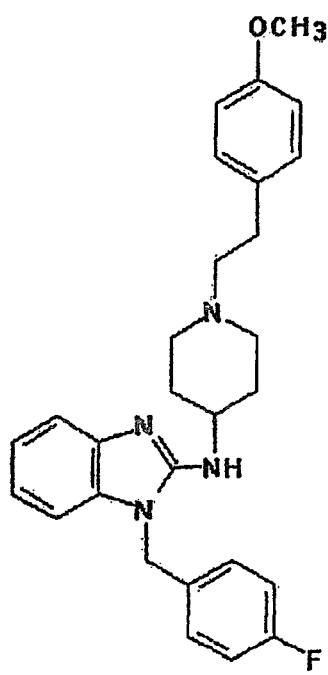
FIG. 1 shows the chemical structure of astemizole (AST), one of the compounds found useful in accordance with the present invention.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the term "neoplasia" is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, including metastatic prostate cancer, testis, bladder, renal, brain/CNS, head and neck, throat, Hodgkin's disease, non-Hodgkin's lymphoma, multiple myeloma, leukemia, melanoma skin cancer, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated using the method of the invention, administering one or more compounds in accordance with the present invention.

The following terms are used to describe the present invention. In instances where a term is not specifically defined herein, that term is given an art-recognized meaning by those of ordinary skill applying that term in context to its use in describing the present invention.

The term "compound" (also "agent"), as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and alternative pharmaceutically acceptable salts (ie., a pharmaceutically acceptable salt form alternative to a pharmaceutically acceptable salt described) and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for the treatment of cancer, especially including prostate cancer and in particular, hormone refractory prostate cancer.

The term "effective" is used herein, unless otherwise indicated, to describe an amount of a compound or composition which, in context, is used to produce or effect an intended result, whether that result relates to the inhibition of the effects of a toxicant on a subject or the treatment of a subject for secondary conditions, disease states or manifestations of exposure to toxicants as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer or refractory cancer, including improvement in the condition through lessening or suppression of at least one symptom, inhibition of cancer growth, reduction in cancer cells or tissue, prevention or delay in progression of metastasis of the cancer, prevention or delay in the onset of disease states or conditions which occur secondary to cancer or remission or cure of the cancer, among others.

"Treatment", as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

In certain particular aspects of the present invention, the cancer which is treated is prostate cancer or hormone refractory prostate cancer. It is understood that metastatic cancer may be found in virtually all tissues of a cancer patient in late stages of the disease, for example, metastatic prostate cancer is found in seminal vesicles, lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology.

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

For this application, the treatment of hormone-sensitive and hormone refractory prostate cancer cells in culture are used as examples, these examples providing evidence sufficient to support use in the treatment of other cancers using the method described herein, and further using these agents for chemoprevention, which includes treatment for persons in high risk groups, such as those genetically prone to develop cancer and persons that have been exposed to conditions that may promote cancer development, neo-adjuvant and adjuvant chemotherapy for cancer, and treatment of all stages of cancer after diagnosis. The method includes use of the identified agents alone as well as in combination with each other. Also, the method allows for these agents to be administered in combination with, or as supplements to, other medical treatments. For example, they may be used in combination with radiotherapy to increase the efficiency of cancer treatment.

The use of specific chemotherapeutic regimens for cancer can depend on the stage of cancer at the time the disease is diagnosed or the state to which the disease has progressed. For example, the initial chemotherapeutic treatment of prostate cancer is often performed using drugs that inhibit androgen production. After 2 to 3 years, prostate cancer becomes refractory to anti-androgen therapy necessitating the use of drugs that non-specifically attack prostate cancer. However, the current treatments for advanced, hormone-refractory prostate cancer do not greatly increase life-span and their actions are largely palliative. Therefore, novel, effective treatments for many cancers, including refractory prostate cancer, are desperately needed.

The term "radiation therapy" is used to describe therapy for prostate cancer which may be used in conjunction with the present compounds which exhibit activity as radiation sensitizers, in addition to their inherent anticancer activity. Radiation therapy uses high doses of radiation, such as X-rays, to destroy cancer cells. The radiation damages the genetic material of the cells so that they can't grow. Although radiation damages normal cells as well as cancer cells, the normal cells can repair themselves and function, while the cancer cells cannot.

Radiation therapy may be in combination with the presently claimed compounds, which can function as radiation sensitizers or the therapy (radiation plus compounds of the present invention) may be further combined with hormonal treatment and other treatment as otherwise disclosed herein to treat prostate cancer. Radiation therapy most effective in treating cancers that have not spread outside the prostate. But it also may be used if the cancer has spread to nearby tissue. Radiation is sometimes used after surgery to destroy any remaining cancer cells and to relieve pain from metastatic cancer.

Radiation is delivered in one of two ways. External-beam radiation therapy and branchytherapy. External-beam radiation therapy uses a large machine to aim a beam of radiation at the tumor. After the area of cancer is identified, an ink tattoo no bigger than a pencil tip is placed on the skin of the subject so that the radiation beam can be aimed at the same spot for each treatment. This helps focus the beam on the cancer to protect nearby healthy tissue from the radiation. External radiation treatments usually are done 5 days a week for 4 to 8 weeks. If cancer has spread to the patient's bones, shorter periods of treatment may be given to specific areas to relieve pain.

There are basically three types of external radiation therapy: conformal radiotherapy (3D-CRT), intensity-modulation radiation therapy (IMRT) and proton therapy. Conformal radiotherapy uses a three-dimensional planning system to target a strong dose of radiation to the prostate cancer. This helps to protect healthy tissue from radiation. Intensity-modulated radiation therapy uses a carefully adjusted amount of radiation. This protects healthy tissues more than conformal radiotherapy does. Proton therapy uses a different type of energy (protons) than X-rays. This approach allows a higher amount of specifically directed radiation, which protects nearby healthy tissues the most, especially the rectum. Sometimes proton therapy is combined with X-ray therapy.

Brachytherapy, or internal radiation therapy, uses dozens of tiny seeds that contain radioactive material. It may be used preferably to treat early-stage prostate cancer. Needles are used to insert the seeds through your skin into your prostate. The surgeon uses ultrasound to locate your prostate and guide the needles. As the needles are pulled out, the seeds are left in place. The seeds release radiation for weeks or months, after which they are no longer radioactive. The radiation in the seeds can't be aimed as accurately as external beams, but they are less likely to damage normal tissue. After the seeds have lost their radioactivity, they become harmless and can stay in place.

Radiation therapy may combine brachytherapy with low-dose external radiation. In other cases, treatment combines surgery with external radiation. In the present invention, compounds which are otherwise claimed may be used as radiation sensitizers.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Anticancer compounds according to the present invention (primary anticancer agents) may be administered with one or more additional (secondary) anti-cancer agents or other agents which are used to treat or ameliorate the symptoms of cancer, especially prostate cancer, including metastatic prostate cancer. Exemplary anticancer agents which may be coadministered in combination with one or more compounds according to the present invention include, for example, antimetabolites, inhibitors of topoisomerase I and II, alkylating agents and microtubule inhibitors (e.g., taxol). Specific anticancer compounds for use in the present invention include, for example, aldesleukin; alemtuzumab; alitretinoin; allopurinol; altretamine; amifostine; anastrozole; arsenic trioxide; asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine(intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

In addition to anticancer agents, a number of other agents may be coadministered with primary anticancer compounds according to the present invention in the treatment of cancer, especially prostate cancer, including metastatic prostate cancer. These include active agents, minerals, vitamins and nutritional supplements which have shown some efficacy in inhibiting prostate cancer tissue or its growth or are otherwise useful in the treatment of prostate cancer. For example, one or more of dietary selenium, vitamin E, lycopene, soy foods, vitamin D, green tea (e.g., extract), omega-3 fatty acids and phytoestrogens, including beta-sitosterol, may be utilized in combination with the present compounds to treat prostate cancer, especially refractory prostate cancer and metastatic prostate cancer.

In addition, active agents, other than traditional anticancer agents have shown some utility in treating prostate cancer. The selective estrogen receptor modulator drug toremifene may be used in combination with the present compounds to treat cancer, especially prostate cancer, including metastatic prostate cancer. In addition, two medications which block the conversion of testosterone to dihydrotestosterone, finasteride and dutasteride, are also useful in the treatment of prostate cancer when coadministered with compounds according to the present invention. The phytochemicals indole-3-carbinol and diindolylmethane, may also be coadministered with the present compounds for their effects in treating prostate cancer. Additional agents which may be combined with compounds according to the present invention include antiandrogens, for example, flutamide, bicalutamide, nilutamide, and cyproterone acetate as well as agents which reduce the production of adrenal androgens (e.g. DHEA), such as ketoconazole and aminoglutethimide. Other active agents which may be combined with compounds according to the present invention include, for example, GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin, among others. These agents may be combined with compounds according to the present invention in effective amounts. In addition, abiraterone acetate may also be combined with one or more compounds according to the present invention in the treatment of prostate cancer, especially including metastatic prostate cancer.

Other agents which may be combined with one or more compounds according to the present invention, include the bisphosphonates such as zoledronic acid, which have been shown to delay skeletal complications such as fractures which occur with patients having metastatic prostate cancer. Alpharadin, another agent, may be combined with compounds according to the present invention to target bone metastasis. In addition, bone pain due to metastatic prostate cancer may be treated with opioid pain relievers such as morphine and oxycodone, among others, which may be combined with compounds according to the present invention.

Coadministration may also refer to the administration of radiation therapy in combination with one or more compounds according to the present invention which may also serve as radiation sensitizers in addition to anticancer agents, optionally in combination with an addition anticancer agent or other agent as described herein which is useful for treating prostate cancer.

The ability of the agents identified herein, for use in the method of the invention, to kill cancer cells was determined by the ability of the agents to induce intracellular granularity. To illustrate the utility of these agents, prostate cancer cell lines were used under conditions that were optimal for induction of markers of intracellular, secretory granules. The identification of agents that induce intracellular granularity in cancer cells as an indicator of agents useful for cancer treatment is entirely novel. High-throughput methods were integrated to efficiently identify chemicals that induce intracellular granularity in prostate cancer cell lines.

Using these methods, the Prestwick chemical library was screened for agents that lead to an increase in intracellular granularity of prostate cancer cells. In addition to detecting increases in intracellular granularity, this methodology detects cell death by identifying chemicals that cause the adherent cells in this assay to become non-adherent. Multiple chemicals have been identified using this technology that are believed to be useful for the prevention and treatment of cancer.

Table 1 includes those chemicals that increase intracellular granularity leading to cancer cell death. It was determined that after reaching peak concentrations of these agents for producing intracellular granularity, these chemicals can lead to cancer cell death. Low doses of these agents cause increased intracellular granularity, which ultimately lead cells to become non-adherent, reducing cell numbers because of cancer cell death (see FIG. 3). For each of these groups, compounds have been selected to test to confirm their efficacy. These compounds may be combined for greater efficacy.

TABLE I compounds that increase intracellular granularity and which cause cancer cell death (primary anti-cancer agents according to the present invention):

3-hydroxymethyl-beta-carboline
Albendazole
Alprenolol hydrochloride
Ambroxol hydrochloride
Amitryptiline hydrochloride
Amodiaquin dihydrochloride dihydrate
Amoxapine
Antazoline hydrochloride
Anisomycin
Antimycin A
Apomorphine hydrochloride
Astemizole
Azacyclonol
Benperidol
Benzethonium chloride
Benzydamine hydrochloride
Bepridil hydrochloride
Bromperidol
Cephaeline dihydrochloride heptahydrate
Chelidonine monohydrate
Chloropyramine hydrochloride
Chlorotrianisene
Chlorpromazine hydrochloride
Chlorprothixene hydrochloride
Chrysene-1,4-quinone
Clomiphene citrate
Clomipramine hydrochloride
Corticosterone
Cyclobenzaprine hydrochloride
Cyproheptadine hydrochloride
Diaziquone
Dibucaine
Dienestrol
Digitoxigenin
Digoxin
Dihydroergocristine mesylate
Dihydroergotoxine mesylate
Domperidone
Doxepin hydrochloride
Emetine dihydrochloride
Epiandrosterone
Ethisterone
Fenbendazole
Fendiline hydrochloride
Fluoxetine hydrochloride
Fluphenazine dihydrochloride
GBR 12909 dihydrochloride
Gossypol
Gramicidin
7-benzyloxy Gramine
Haloprogin
Harmaline hydrochloride dehydrate
Hycanthone
Ifenprodil tartrate
Imipramine hydrochloride
Ketotifen fumarate
Lanatoside C
Lidoflazine
Loperamide hydrochloride
Maprotiline hydrochloride
Mebendazole
Mebhydroline 1,5-naphtalenesulfonate
Menadione
Mesoridazine besylate
Metergoline
Methimazole
Methiothepin maleate
Methotrimeprazine maleate salt
Metixene hydrochloride
Mycophenolic acid
Niclosamide
Nitrarine dihydrochloride
Nocodazole
Norcyclobenzaprine
Norethynodrel
Nortriptyline hydrochloride TABLE I-continued compounds that increase intracellular granularity and
which cause cancer cell death (primary anti-cancer agents
according to the present invention):

Parthenolide
Perphenazine
Pemexiline maleate
Pimozide
Piperlongumine
Phenoformin hydrochloride
Primaquine diphosphate
Prochlorperazine dimaleate
Propafenone hydrochloride
Pyrimethamine
Quinacrine dihydrochloride dihydrate
Quinidine hydrochloride monohydrate
Remerine hydrochloride
Rescinnamin
Securinine
Scoulerine
Solanine alpha
Strophanthidin
Suloctidil
Tacrine hydrochloride hydrate
Terconazole
Terfenadine
Thimerosal
Thioridazine hydrochloride
1-phenyl-3-(2-thiazolyl)-2-Thiourea
Triamterene
Trifluoperazine dihydrochloride
Triflupromazine hydrochloride
Trimeprazine tartrate
Trimipramine maleate salt
Ursolic acid
Zimelidine dihydrochloride monohydrate One chemical, astemizole (AST), was chosen for more detailed study. AST has the IUPAC name 1-[(4-fluorophenyl) methyl]-N-[1-[2-(4-ethoxyphenyl)ethyl]-4-piperidyl]benzoimidazol-2-amine, CAS number 68844-77-9, chemical formula $C_{28}H_{31}FN_4O$, mol. mass 458.571. It was discovered that human cancer cells, as for example prostate cancer cells, cultured with AST at concentrations above 5 µM undergo rapid cell death. Previous reports have described the therapeutic value of AST, but there are no reports of therapeutic value related to cancer treatment.

For example, it is known that AST acts as a histamine H1-receptor antagonist with a long duration of action. In this regard, AST acts to suppress actions mediated by histamine, such as edema and pruritus manifesting anticholinergic and antipruritic effects. AST competitively binds to histamine H1-receptor sites in the gastrointestinal tract, uterus, blood vessels, and bronchial muscle. Pharmacokinetically, AST is rapidly absorbed from the gastrointestinal tract; protein binding is around 96%. AST does not cross the blood-brain barrier and H1 receptor binding is mostly in the peripheral rather than central nervous system. There is nothing which would lead one to believe that AST could be an effective agent for the treatment of cancer.

Materials and Methods

Chemicals: Initial screens were performed using chemicals present in the Prestwick Chemical Library (Illkirch, France). Follow up studies, including those performed with astemizole (Sigma-Aldrich Cat. No. A6424), used chemicals acquired from Sigma-Aldrich Chemical Co. (St. Louis, Mo.), unless specified otherwise. The chemical structure of astemizole is shown in FIG. 1.

Cell Culture: The androgen-sensitive CWRv22 (i.e., 22Rv1) and LNCaP as well as the androgen-independent DU145 and PC3 human prostate cancer cell lines were acquired from American Type Culture Collection (Manassas, Va.). All cell lines were maintained in Dulbecco's modified Eagle's medium (DMEM; Invitrogen, Carlsbad, Calif.) containing 5% heat-inactivated fetal calf serum (FCS; Sigma, St. Louis, Mo.) with streptomycin-penicillin antibiotics (designated DMEM/FCS) in a 5% $CO_2$ incubator at 37° C. LAPC4 cells adapted to growth in DMEM and 5% FCS were acquired from George Wilding (University of Wisconsin, Paul P. Carbone Comprehensive Cancer Center).

Cell Proliferation Assay: To determine the number of proliferating cells after astemizole treatment, cells were seeded in 96-well tissue culture plates at 5,000 cells per well in 100 uL of DMEM/FCS. Two days after plating, cells were treated with astemizole at the indicated concentrations. Four days after treatment, cell proliferation was determined using the CyQUANT NF Cell Proliferation Assay Kit (Invitrogen, Carlsbad, Calif.) according to the kit instructions.

Cell Viability Assays: Two assays were used to determine cell viability; propidium iodide exclusion with flow cytometry and trypan blue exclusion with hemacytometry. Cells were treated with astemizole at the indicated concentrations for 24 to 96 hours prior to viability analysis. For propidium iodide cell viability determinations, cells were removed from the dishes with 0.05% trypsin. All cell culture medium was collected for the analysis in order to include any cells that may have released from the plate during the incubation period. Propidium iodide was added at a final concentration of 2 µg/ml and cells were analyzed on a Becton Dickinson FACScan flow cytometer. For trypan blue dye exclusion studies, all cell culture medium and cells removed by trypsinization were collected as above. An aliquot of these cells was resuspended in 0.4% trypan blue. Both viable and non-viable cell counts were obtained by manual counting using a hemacytometer and light microscopy.

HyperCyt and High-throughput Data Analysis: The HyperCyt® cytometry analysis system interfaces a flow cytometer and an autosampler. While the sampling probe moves from well to well, a peristaltic pump sequentially aspirates a small volume from each well. A bubble of air, created by the continuously running pump, separates samples from individual wells. Sample and bubble volumes are determined by the time the sampling probe is in a well (sip time) or in taking air while moving from well to well (up time). HyperCyt® sampling of a single 384-well plate is completed in less than 15 minutes. This system has been validated using cell-based high-throughput endpoint assays for ligand binding, surface antigen expression, and immunophenotyping.

The air-bubble separated samples, collected by HyperCyt®, are delivered continuously to the cytometer. The data accumulates as a single, time-resolved file with gaps corresponding to air-bubbles. Both forward and side light scattering properties of treated LNCaP cells were measured using a 488 nm laser. Time-resolved data were analyzed by proprietary software (IDLQuery) set to search for 384 separate data clusters. Data from negative (0.1% DMSO) replicate wells were pooled and used to set gates that define granularity in vehicle-treated LNCaP cells. Negative control samples were defined as an LNCaP population where 10% of the cells exhibit increased granularity based on side scatter properties. A gate is set reflecting this distinction that is then applied to each data cluster. These values are automatically exported to a Microsoft Excel spreadsheet template that calculates percent side scatter shift in individual treated samples.

Microscopic and Flow Cytometric Scatter Analysis: Light microscopy images of prostate cancer cells in culture were collected using an Olympus IX70 inverted microscope and a 20× objective. Flow cytometric analysis of forward scatter (FSC) and side scatter (SSC) were preformed using the UNM Shared Flow Cytometry Resource on a Cytomation Mo Flo, an Epics Elite, a Becton Dickinson FACScan, or a Becton Dickinson FACS Calibur.

Results

Figure 2:
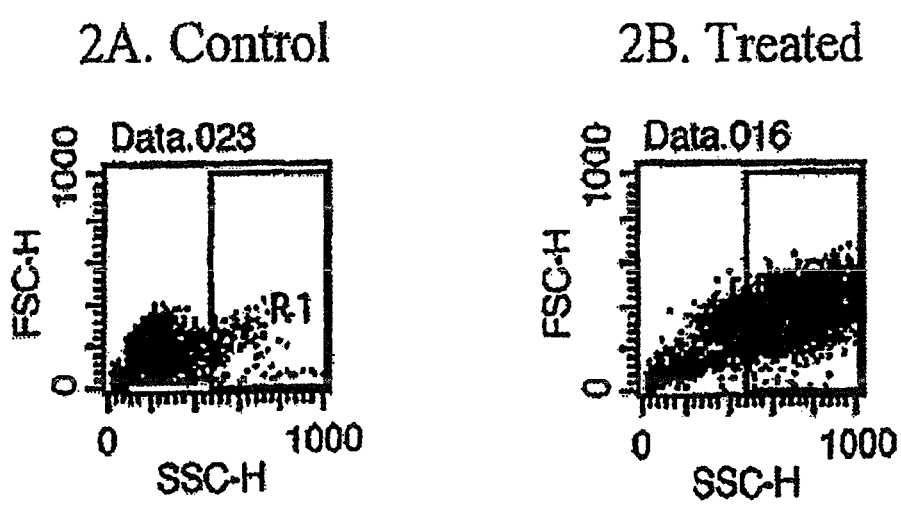
FIGS. 2A and 2B are flow cytometric analyses of prostate cancer cells used to measure levels of intracellular granularity using side scatter (SSC-H) as an endpoint. Untreated, control cells are shown in FIG. 2A with low SSC-H levels present in the gated region R1, whereas high intra-cellular granularity is seen in treated cells as shown in FIG. 2B.
Figure 3:
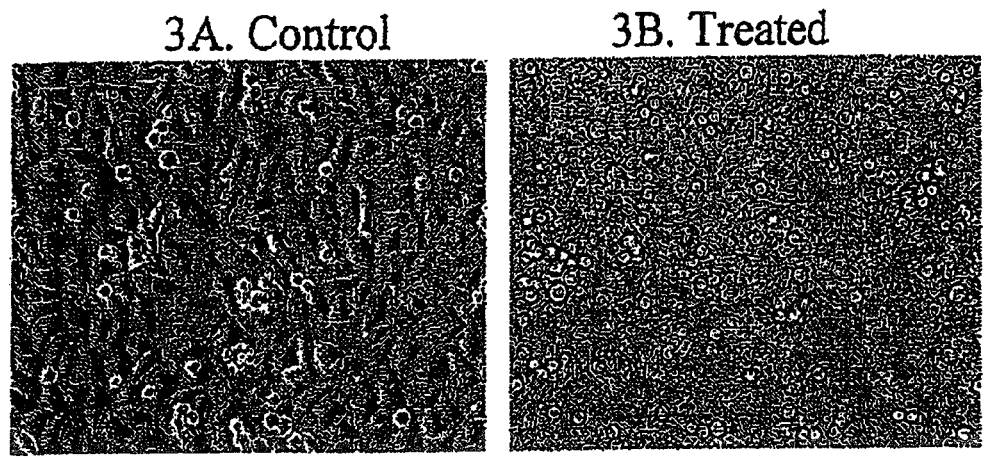
FIG. 3 shows 200X phase contrast microscopy images showing increased intracellular granularity of treated PC3 human prostate cancer cells.

High-throughput methods were developed using the HyperCyt system and flow cytometry to efficiently identify agents that induce cancer cells to express markers of increased intracellular granularity. To achieve this goal, flow cytometry using side-scatter (SSC) as an endpoint is a sensitive method to examine cells for levels of intracellular granularity. Astemizole (AST) was chosen as a representative agent from Table 1 to characterize more fully for the induction of intraceullar granularity and cancer cell death. Using SSC measured by flow cytometry, astemizole (AST) was found to significantly increase cancer cell intracellular granularity (FIG. 2). The increase in intracellular granularity in cancer cells can be directly observed in PC3 human prostate cancer cells by light microscopy (FIG. 3). An increase in cancer cell intracellular granularity was found to be a predictive marker of agents that ultimately result in cancer cell death.

Figure 4:
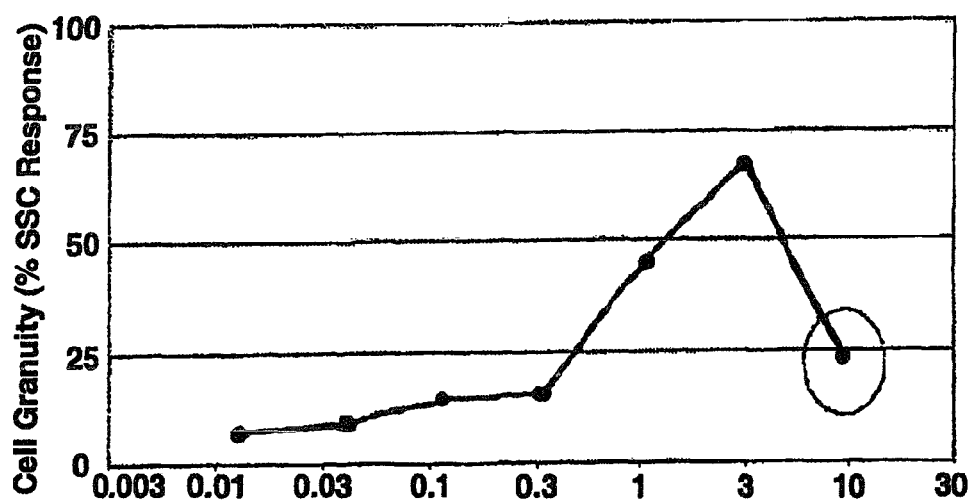
FIG. 4 shows a dose-response for induction of intracellular granularity followed by prostate cancer cell death. Cell death is shown circled at 10 µM.

Use of the HyperCyt flow cytometry system allows for the detection of cell death by identifying compounds that cause adherent cancer cells in the assay to become non-adherent when they die. This is illustrated in FIG. 4 showing a dose-response for AST-induced increases in intracellular granularity (i.e., up to 3 µM), which is followed by cell death seen at a dose of 10 µM. The action of AST on cancer cells to induce intracellular granularity and cell death has not previously been observed.

Figure 5:
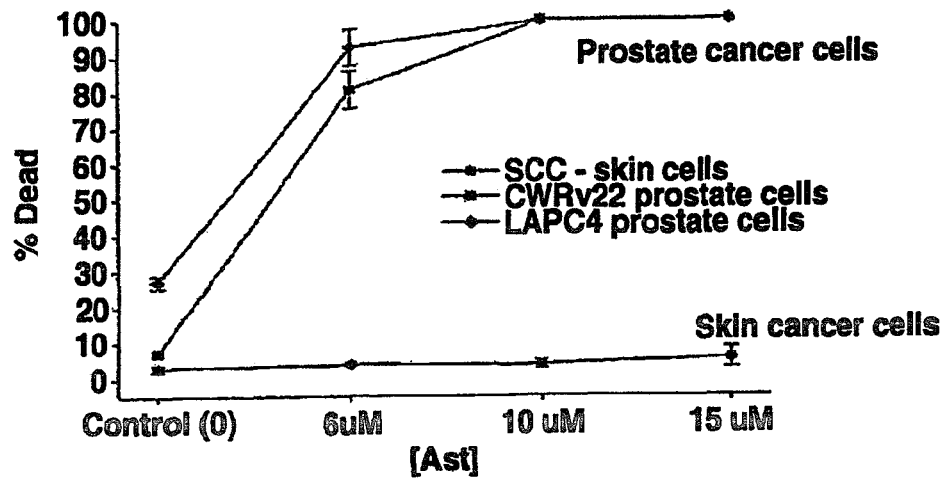
FIG. 5 shows cell death measured in CWRv22 and LAPC4 human prostate cancer cell lines using trypan blue uptake and hemacytometry. SCC cells are a skin cancer cell line that were not killed by treatment with AST up to 15 µM.

Cell killing is the most important endpoint for agents targeted at cancer treatment. Multiple prostate cancer cell lines were used to determine cytotoxicity of AST in culture on cancer cells. The action of AST against the androgen-sensitive LNCaP, LAPC4, and CWRv22 human prostate cancer cells lines was evaluated and found to show a dose-response to cell killing by AST treatment. For example, as shown in FIG. 5, CWRv22 and LAPC4 human prostate cancer cells were treated with 6, 10, and 15 µM AST for 24 hours and the number of non-viable cells was determined by trypan blue uptake and hemacytometry. Both CWRv22 and LAPC4 were highly sensitive to AST even at the lowest dose tested of 6 µM where 80% of the cells were dead within 24 hours of treatment. In contrast, skin cancer cells (SCC) were found to be resistant to cell death by AST treatment (FIG. 5).

Figure 6:
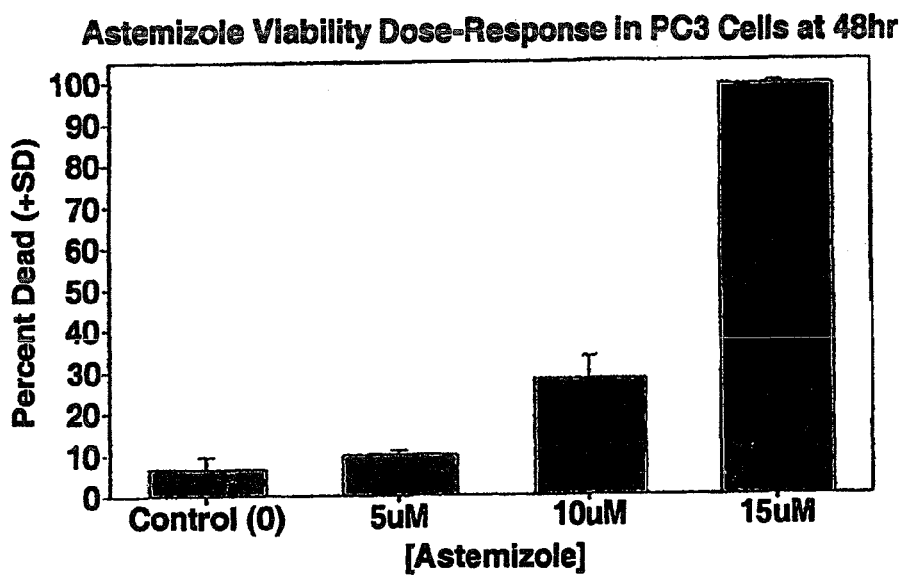
FIG. 6 shows cell death measured in PC3 androgen-independent human prostate cancer cells using trypan blue uptake and hemacytometry.
Figure 7:
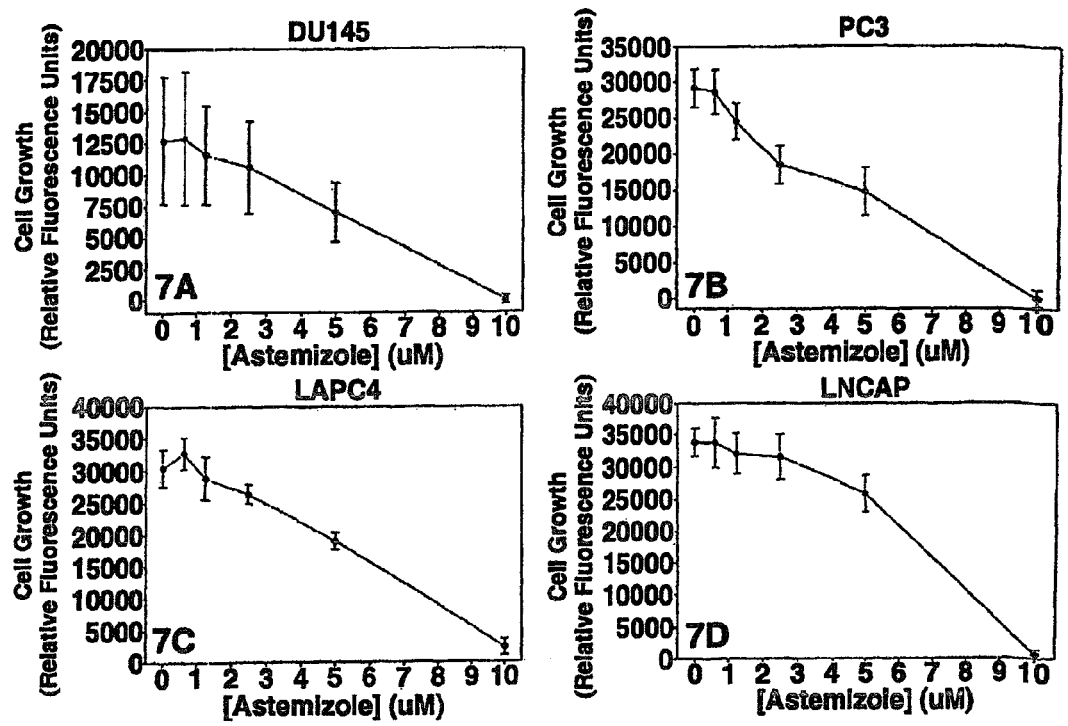
FIG. 7 shows a cell growth analysis in multiple prostate cancer cell lines treated with astemizole, FIG. 7A with DU145 cells, FIG. 7B with PC3 cells, FIG. 7C with LAPC4 cells, and FIG. 7D with LNCaP cells.

In addition to inducing cell death in androgen-sensitive cell lines described above, AST was equally effective at inducing cell death in the androgen-independent PC3 cell line (FIG. 6). PC3 prostate cancer cells were evaluated for induction of cell death after treatment with AST at 5, 10, and 15 µM for 48 hours (FIG. 6) as measured by trypan blue uptake. In this study, greater than 25% cell death was observed in PC3 cells treated with 10 for 48 hours. Importantly, nearly 100% of PC3 cells were dead following treatment with 15 µM AST (FIG. 6). AST inhibited the growth of PC3 cells over a 4 day period at concentrations as low as 1 uM AST (FIG. 7). The significant reduction in prostate cancer cell growth induced by AST was observed in DU145, LAPC4, and LNCaP human prostate cancer cells (FIG. 7). Therefore, AST was found to be a potent inhibitor of prostate cancer cell growth among all cell lines tested and at higher concentrations, AST treatment resulted in prostate cancer cell death.

Figure 8:
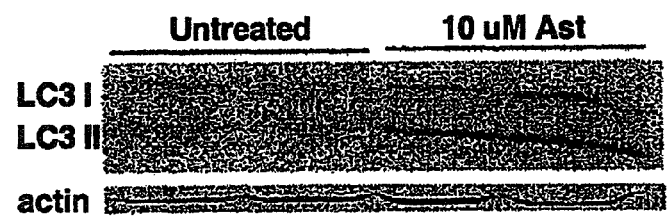
FIG. 8 shows the induction of an LC3 II band in CWRv22 cells by 10 µM astemizole, indicating that autophagy is induced in these cells.

Multiple mechanisms could account for the cell death observed in cancer cells from treatment with AST. Cell death in PC3 cells occurs within 24 hours of treatment but it does not produce hallmarks of apoptotic cell death, such as the production of a hypodiploid population of cells as measured using propidium iodide incorporation and flow cytometry. Intriguingly, CWRv22 prostate cancer cells treated with 10 µM AST for 6 hours show an increase in the LC3 II band associated with autophagic pathways (FIG. 8). Thus, administering the agents identified above that induce intracellular granularity in cancer cells may produce cell death through an autophagic mechanism.

As to the use of astemizole itself as the agent selected from Table 1, pharmacokinetic studies in man demonstrated that astemizole is rapidly absorbed, peak plasma concentrations being attained within 1 to 4 hours. Astemizole is extensively metabolized, and excreted as metabolites chiefly in the feces. The half-life of the active ingredient is approximately 1 day and the elimination half-life of the active metabolites is 10 to 14 days. Astemizole was originally indicated for the treatment of allergic rhinitis, allergic conjunctivitis and chronic urticaria, though it was removed from the U.S. market in 1999. More recently, astemizole has been found to be a potent anti-malarial. The recommended administration would be in an oral form, such as by way of 10 mg tablets, one such administration being of from 1-30 mg per day, depending on the particulars of the patient to whom the dosage would be administered, more preferably being at from 5-20 mg. per day. Optimal absorption is achieved when taken on an empty stomach. Although overdoses have been reported with no ill effects, rare cases of serious life-threatening cardiovascular adverse events including QT-prolongation, torsades de pointes, and other ventricular arrhythmias have been observed in patients exceeding recommended doses of astemizole. It is believed that similar dosages of the other compounds from Table 1 can be readily determined, the dosage for astemizole being illustrative thereof.

Compounds according to the present invention may also function as radiosensitizers in addition to their anticancer activity. A study was performed showing prostate cancer cell killing actions of astemizole in combination with other therapeutic interventions. Astemizole alone produced a decrease in 22Rv1 prostate cancer cell viability with 8 µM 24 hours after treatment. In combination with 10 nM docetaxel, 2, 4, and 8 µM astemizole showed additive levels of cell killing after 24 hours. In combination with 10 gray radiation, 2, 4, and 8 µM astemizole showed synergistic levels of cell killing after 24 hours. The results are set forth in the table presented hereinbelow. These studies show that astemizole acts as a radiosensitizer making prostate cancer cells more susceptible to the cell killing effects of ionizing radiation. This is true of the other agents which are described herein.

TABLE 1

| | % Viability* | | | |
| --- | --- | --- | --- | --- |
| | [Astemizole] (µM) - Mean (SD) | | | |
| Treatment | 0 | 2 | 4 | 8 |
| Control | 89.7 (2.2) | 88.2 (4.9) | 90.6 (1.2) | 64.3 (8.1) |
| 10 nM docetaxel | 80.7 (1.7) | 71.3$^\&$ (4.1) | 74.4$^\&$ (4.0) | 49.7$^\&$ (5.5) |
| 10 Gy radiation | 69.3 (4.2) | 63.5$^\&$ (1.1) | 57.4$^\#$ (2.6) | 22.2$^\#$ (1.2) |

*Viability in 22Rv1 prostate cancer cells determined 24 h after treatment by trypan blue exclusion; n = 3.
$^\&$Additive action determined with combination therapy.
$^\#$Synergistic action determined with combination therapy.

It is noted that, as used in this specification and the appended claims, the singular forms "a," "an," and "the," include plural referents unless expressly and unequivocally limited to one referent. Thus, for example, reference to "a cell" includes two or more different cells. As used herein, the term "include" and its grammatical variants are intended to be non-limiting, such that recitation of items in a list is not to the exclusion of other like items that can be substituted or other items that can be added to the listed items.

The method of the invention contemplates the administration of an agent which causes increased intracellular granularity in cancer cells, at least in an amount sufficient to inhibit proliferation of such cells and preferably in an amount sufficient to lead to cancer cell death, but more preferably as a pharmaceutical composition, which can be formulated using know methods to adapt the agent for administration via known routes, such as topically, orally, transdermally, rectally, vaginally, parentally, intranasally, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation. Thus, the compounds according to the invention may be formulated for administration in any convenient way for use in human or veterinary medicine, and formulated into pharmaceutically acceptable dosage forms such as described below or by other conventional methods known to those of skill in the art.

The method of the invention thus includes administering pharmaceutically acceptable compositions containing a therapeutically effective amount of an agent which causes increased intracellular granularity in cancer cells, which may be one or more of the compounds described above in Table 1, formulated together with one or more pharmaceutically acceptable carriers and/or diluents. The pharmaceutical compositions may be formulated for administration in solid or liquid form, and adapted for oral administration, as aqueous or non-aqueous solutions or suspensions, tablets, boluses, powders, granules, pastes for application to the tongue or adapted for parenteral administration by subcutaneous, intramuscular or intravenous injection. Topical applications by way of a cream, ointment or spray may be of particular interest in countering the effects of toxicants, post exposure, as well as formulations that are administered via inhalation.

The phrase "therapeutically effective amount" as used herein means that amount of a compound, material, or composition which is effective for producing a desired therapeutic effect by increasing intracellular granularity in cancer cells, and/or converting adherent cancer cells to non-adherent cancer cells, leading to cancer cell death, at least in an amount sufficient to inhibit proliferation of such cells and preferably in an amount sufficient to lead to cancer cell death in at least a sub-population of cells in an animal and thereby blocking the biological consequences of that function in the treated cells, at a reasonable benefit/risk ratio applicable to any medical treatment.

"Pharmaceutically acceptable" as used herein means that the compound or composition is suitable for administration to a subject to achieve the treatments described herein, without unduly deleterious side effects in light of the severity of the disease and necessity of the treatment.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient.

It should be understood that various additives, such as wetting agents, emulsifiers and lubricants, as well as coloring agents, release agents, coating agents, sweetening, flavoring and perfuming agents, preservatives and antioxidants can also be present in the compositions administered according to the present invention.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles and/or as mouth washes and the like, each containing a predetermined amount of the agent which causes increased intracellular granularity in cancer cells, at least in an amount sufficient to inhibit proliferation of such cells and preferably in an amount sufficient to lead to cancer cell death, as an active ingredient. Of course, the composition can be formulated so as to provide slow or controlled release of the active ingredient using known pharmacological procedures, such as, for example, hydroxypropylmethyl cellulose in varying proportions to provide the desired release profile.

Topical or transdermal administration may be by way of applying powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required. Ophthalmic formulations in the form of eye ointments, powders, solutions and the like, may also be used in the method of the invention.

The method of the invention contemplates the administration of the agent which causes increased intracellular granularity in cancer cells as the active ingredient, as pharmaceuticals to humans and animals, administered per se or as a pharmaceutical composition containing, for example, 0.1 to 99.5% (more preferably, 0.5 to 90%) of the active ingredient in combination with a pharmaceutically acceptable carrier. Actual dosage levels of the active ingredient may be varied so as to obtain an amount of the active ingredient that is effective to achieve the desired therapeutic response from an individual patient, and given the choice of agent, mode of administration, etc.

The actual dosage depends upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts, and it is within the ordinary skill of a physician to determine the effective dose.

In general, a suitable daily dose of a compound of the invention will be that amount of the compound that is the lowest dose effective to produce a therapeutic effect. Such an effective dose will generally depend upon the factors described above. Generally, doses will range from about 0.0001 to about 100 mg per kilogram of body weight per day.

The patient receiving this treatment is any animal in need, including primates, in particular humans, and other mammals such as equines, cattle, swine and sheep; and poultry and pets in general.

"Treat", "treating", and "treatment", etc., as used herein, refer to any action providing a benefit to a patient at risk for or afflicted by cancer, including improvement in the condition through lessening or suppression of at least one symptom, delay in progression of the effects of the cancer, prevention or delay in the onset of the effects of the cancer, etc. Treatment, as used herein, encompasses both prophylactic and therapeutic treatment.

As discussed above, for example, the agents which cause increased intracellular granularity in cancer cells, at least in an amount sufficient to inhibit proliferation of such cells and preferably in an amount sufficient to lead to cancer cell death, and so can be administered prophylactically to a mammal in advance of the initiation or proliferation of such cancer. Prophylactic administration is effective to decrease the likelihood of the occurrence of disease in the mammal.

It will be apparent to those skilled in the art that various modifications and variations can be made in the devices and methods of the present disclosure. Other embodiments of the disclosure will be apparent to those skilled in the art from consideration of the specification and practice of the embodiments disclosed herein. It is intended that the specification and examples be considered as exemplary only.

The complete disclosure of all patents, patent applications, and publications, and electronically available material cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of treating cancer in a human patient with cancer in need comprising administering to said patient a composition comprising a therapeutically effective amount of securinine and/or pharmaceutically acceptable salt thereof and wherein said cancer is lung cancer, breast cancer, colon cancer, rectal cancer, brain/CNS cancer, liver cancer, ovarian cancer, pancreatic cancer and prostate cancer.

2. The method according to claim 1 wherein said composition further comprises at least one secondary anticancer agent.

3. The method according to claim 1 wherein said composition is coadministered with an effective amount of at least one secondary anticancer agent.

4. The method according to claim 2 wherein said at least one secondary anticancer agent is selected from the group consisting of selected from the group consisting of antimetabolites, inhibitors of topoisomerase I and II, alkylating agents, microtubule inhibitors and mixtures thereof.

5. The method according to claim 2 wherein said at least one secondary anticancer agent is aldesleukin; alemtuzumab; alitretinoin; allopurinol; altretamine; amifostine; anastrozole; arsenic trioxide; asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a ; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; or a mixture thereof.

6. The method according to claim 3 wherein said at least one secondary anticancer agent is selected from the group consisting of selected from the group consisting of antimetabolites, inhibitors of topoisomerase I and II, alkylating agents, microtubule inhibitors and mixtures thereof.

7. The method according to claim 3 whereien said at least one secondary anticancer agent is aldesleukin; alemtuzumab; alitretinoin; allopurinol; altretamine; amifostine; anastrozole; arsenic trioxide; asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; or a mixture thereof.

8. The method according to claim 1 which is used in combination with radiation therapy.

9. The method according to claim 2 which is used in combination with radiation therapy.

10. The method according to claim 3 which is used in combination with radiation therapy.

11. The method according to claim 4 which is used in combination with radiation therapy.

12. The method according to claim 5 which is used in combination with radiation therapy.

13. The method according to claim 6 which is used in combination with radiation therapy.

14. The method according to claim 7 which is used in combination with radiation therapy.

15. The method according to claim 1 wherein said cancer is breast cancer, colon cancer, rectal cancer, brain/CNS cancer, liver cancer, ovarian cancer, pancreatic cancer and prostate cancer and wherein said lung cancer is small cell lung cancer.

16. The method according to claim 2 wherein said cancer is breast cancer, colon cancer, rectal cancer, brain/CNS cancer, liver cancer, ovarian cancer, pancreatic cancer and prostate cancer and wherein said lung cancer is small cell lung cancer.

17. The method according to claim 3 wherein said cancer is breast cancer, colon cancer, rectal cancer, brain/CNS cancer, liver cancer, ovarian cancer, pancreatic cancer and prostate cancer and wherein said lung cancer is small cell lung cancer.

18. The method according to claim 4 wherein said cancer is breast cancer, colon cancer, rectal cancer, brain/CNS cancer, liver cancer, ovarian cancer, pancreatic cancer and prostate cancer and wherein said lung cancer is small cell lung cancer.

19. The method according to claim 5 wherein said cancer is breast cancer, colon cancer, rectal cancer, brain/CNS cancer, liver cancer, ovarian cancer, pancreatic cancer and prostate cancer and wherein said lung cancer is small cell lung cancer.

20. The method according to claim 6 wherein said cancer is breast cancer, colon cancer, rectal cancer, brain/CNS cancer, liver cancer, ovarian cancer, pancreatic cancer and prostate cancer and wherein said lung cancer is small cell lung cancer.

21. The method according to claim 7 wherein said cancer is breast cancer, colon cancer, rectal cancer, brain/CNS cancer, liver cancer, ovarian cancer, pancreatic cancer and prostate cancer and wherein said lung cancer is small cell lung cancer.

22. The method according to claim 8 wherein said cancer is breast cancer, colon cancer, rectal cancer, brain/CNS cancer, liver cancer, ovarian cancer, pancreatic cancer and prostate cancer and wherein said lung cancer is small cell lung cancer.

23. The method according to claim 9 wherein said cancer is breast cancer, colon cancer, rectal cancer, brain/CNS cancer, liver cancer, ovarian cancer, pancreatic cancer and prostate cancer and wherein said lung cancer is small cell lung cancer.

24. The method according to claim 10 wherein said cancer is breast cancer, colon cancer, rectal cancer, brain/CNS cancer, liver cancer, ovarian cancer, pancreatic cancer and prostate cancer and wherein said lung cancer is small cell lung cancer.

25. The method according to claim 1 wherein said composition is administered to said patient orally.

26. The method according to claim 1 wherein said composition is administered to said patient parenterally.

27. A method of treating cancer in a human patient with cancer in need comprising administering to said patient a therapeutically effective amount of a composition comprising securinine and/or a pharmaceutically acceptable salt thereof as the sole agent(s) causing increased intracellular granularity and/or converting adherent cancer cells to non-adherent cancer cells leading to cancer cell death in said patient, optionally in combination with at least one secondary anticancer agent and wherein said cancer is lung cancer, breast cancer, colon cancer, rectal cancer, brain/CNS cancer, liver cancer, ovarian cancer, pancreatic cancer and prostate cancer.

28. The method according to claim 26 wherein said at least one secondary anticancer agent is aldesleukin; alemtuzumab; alitretinoin; allopurinol; altretamine; amifostine; anastrozole; arsenic trioxide; asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; or a mixture thereof.

29. The method according to claim 27 wherein said cancer is breast cancer, colon cancer, rectal cancer, brain/CNS cancer, liver cancer, ovarian cancer, pancreatic cancer and prostate cancer and wherein said lung cancer is small cell lung cancer.

* * * * *